(12) United States Patent
Heuvel et al.

(10) Patent No.: US 10,065,035 B2
(45) Date of Patent: *Sep. 4, 2018

(54) FLEXIBLE PROTOCOL FOR AN IMPLANTED PROSTHESIS

(71) Applicant: Cochlear Limited, Macquarie University, NSW (AU)

(72) Inventors: Koen Van den Heuvel, Hove (BE); Koen Van Herck, Kontich (BE)

(73) Assignee: Cochlear Limited, Macquarie University, NSW (AU)

( * ) Notice: Subject to any disclaimer, the term of this patent is extended or adjusted under 35 U.S.C. 154(b) by 100 days.

This patent is subject to a terminal disclaimer.

(21) Appl. No.: 15/059,647

(22) Filed: Mar. 3, 2016

(65) Prior Publication Data
US 2016/0184587 A1 Jun. 30, 2016

Related U.S. Application Data

(63) Continuation of application No. 13/268,017, filed on Oct. 7, 2011, now Pat. No. 9,326,075.

(51) Int. Cl.
*H04R 25/00* (2006.01)
*A61N 1/36* (2006.01)
*A61N 1/372* (2006.01)

(52) U.S. Cl.
CPC ....... *A61N 1/36032* (2013.01); *A61N 1/3606* (2013.01); *A61N 1/3727* (2013.01); *A61N 1/37252* (2013.01); *A61N 1/37264* (2013.01); *H04R 25/30* (2013.01)

(58) Field of Classification Search
CPC .............. A61N 1/37264; A61N 1/3727; A61N 1/32752; A61N 1/3606; H04R 25/00–25/75
See application file for complete search history.

(56) References Cited

U.S. PATENT DOCUMENTS

| | | |
|---|---|---|
| 5,597,380 A | 1/1997 | McDermott |
| 5,741,314 A | 4/1998 | Daly |
| 6,219,580 B1 | 4/2001 | Faltys |
| 6,594,525 B1 | 7/2003 | Zierhofer |
| 6,600,955 B1 | 7/2003 | Zierhofer |
| 7,072,717 B1 | 7/2006 | Wolf |
| 7,088,738 B1 | 8/2006 | Alvarez et al. |
| 7,310,558 B2 | 12/2007 | Van Hoesel |
| 8,194,901 B2 | 6/2012 | Alber et al. |

(Continued)

FOREIGN PATENT DOCUMENTS

WO 2010045358 A1 4/2010

*Primary Examiner* — Thaddeus Cox
(74) *Attorney, Agent, or Firm* — Edell, Shapiro & Finnan, LLC

(57) ABSTRACT

The present application discloses systems and methods for transmitting configuration between a command module and a stimulation module of a hearing prosthesis. In accordance with at least some embodiments of the disclosed systems and methods, a hearing prosthesis determines that a block of configuration data is queued for transmission. In response to this determination, the hearing prosthesis divides the amount of queued configuration data into a plurality of configuration data fragments and transmits the data fragments separately. In some embodiments, the command module appends each configuration data fragment to a different packet of stimulation commands and transmits to the stimulation module appended stimulation packets.

11 Claims, 8 Drawing Sheets

(56) References Cited

U.S. PATENT DOCUMENTS

| | | |
|---|---|---|
| 8,340,331 B2 | 12/2012 | Pansell et al. |
| 8,406,441 B2 | 3/2013 | Ruwisch |
| 2007/0300006 A1 | 12/2007 | Isaacs et al. |
| 2008/0031478 A1 | 2/2008 | Alber et al. |
| 2011/0264155 A1 | 10/2011 | Van den Huevel et al. |

FLEXIBLE PROTOCOL FOR AN IMPLANTED PROSTHESIS

CROSS-REFERENCE TO RELATED APPLICATION

This application is a continuation of U.S. patent application Ser. No. 13/268,017, filed Oct. 7, 2011, now U.S. Pat. No. 9,326,075, the entire contents of which is incorporated herein by reference.

BACKGROUND

Various types of hearing prostheses may provide persons with different types of hearing loss with the ability to perceive sound. Hearing loss may be conductive, sensorineural, or some combination of both conductive and sensorineural hearing loss. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound, and a vibration mechanism to apply vibrations corresponding to the detected sound to a person's bone, thereby causing vibrations in the person's inner ear, thus bypassing the person's auditory canal and middle ear. Vibration-based hearing devices may include bone-anchored hearing devices, direct acoustic cochlear stimulation devices, or other vibration-based devices. A bone-anchored hearing device typically utilizes a surgically-implanted mechanism to transmit sound via direct vibrations of the skull. Similarly, a direct acoustic cochlear stimulation device typically utilizes a surgically-implanted mechanism to transmit sound via vibrations corresponding to sound waves to generate fluid motion in a person's inner ear. Other non-surgical vibration-based hearing devices may use similar vibration mechanisms to transmit sound via direct vibration of teeth or other cranial or facial bones.

Persons with certain forms of sensorineural hearing loss may benefit from cochlear implants and/or auditory brainstem implants. For example, cochlear implants may provide a person having sensorineural hearing loss with the ability to perceive sound by stimulating the person's auditory nerve via an array of electrodes implanted in the person's cochlea. The cochlear implant detects sound waves and converts them into a series of electrical stimulation signals that are delivered to the implant recipient's cochlea via the array of electrodes. Auditory brainstem implants may use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with sensorineural hearing loss to perceive sound.

The effectiveness of any of the above-described hearing prostheses depends not only on the design of the particular prosthesis but also on the prosthesis's particular stimulation strategy (i.e., the manner in which the prosthesis detects acoustic signals and delivers responsive stimulation to the relevant portions of a person's outer ear, cranial or facial bones, teeth, middle ear, inner ear, cochlea, or brainstem). The process of programming a hearing prosthesis with an appropriate set of operation parameters (sometimes referred to as "fitting" or "mapping") is often performed by an audiologist or other similarly-trained specialist typically in an office type setting or other professional setting away from the prosthesis recipient's home.

SUMMARY

Typically, hearing prostheses are arranged such that an external module, or "command module," generates and transmits stimulation commands to an internal module, or "stimulation module." The external module may generate the stimulation commands based on a received acoustic signal and an appropriate stimulation strategy. The internal module may receive the stimulation commands and apply stimulation in accordance with those stimulation commands. Generally, the stimulation commands instruct the stimulation module how to apply stimulation signals to the relevant portions of a person's outer ear, cranial or facial bones, teeth, middle ear, inner ear, cochlea, or brainstem.

At times, the command module has data other than stimulation data to transmit to the stimulation module. This data, sometimes referred to as "configuration data," may be a measurement, readout value, data flag, an indication to change at least one operational parameter, or some other type of data. For reasons discussed further herein, the stimulation module can generally apply stimulation only when receiving stimulation data and not while receiving configuration data. Therefore, the transmission of long blocks of configuration data may delay the transmission of stimulation commands, which in turn may result in a period in which there is no sound perceived by the hearing prosthesis recipient. Generally, periods of no perceived sound are undesirable.

The present application discloses systems and methods to address situations in which a hearing prosthesis has a large block of configuration data to transmit. In accordance with at least some embodiments of the disclosed systems and methods, a hearing prosthesis determines that a block of configuration data is queued for transmission. The hearing prosthesis may make this determination by comparing the amount configuration data to a threshold amount and determining that the amount of queued configuration data is greater than the threshold amount of configuration data. In one embodiment, the threshold amount of configuration data is an amount that, if transmitted in a continuous block, would cause a delay in the transmission of stimulation data and thereby potentially cause an undesirable interruption in perceived sound by the hearing prosthesis recipient.

In response to this determination, the hearing prosthesis divides the amount of queued configuration data into a plurality of configuration data fragments and transmits the data fragments separately. In some embodiments, the command module appends each configuration data fragment to a different packet of stimulation commands and transmits appended stimulation packets to the stimulation module. In one embodiment, the command module divides the configuration data into fragments of a particular size that fit into unused space in a stimulation data packet. In another embodiment, the command module divides the configuration data into fragments of a particular size such that when transmitted, there is an unnoticeable or acceptable interruption in perceived sound by the prosthesis recipient. And in yet another embodiment, the stimulation module divides an amount of configuration data into fragments and transmits the fragments to the command module after reception of a stimulation packet.

DETAILED DESCRIPTION

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

Certain aspects of the disclosed systems, methods, and articles of manufacture may be described herein with reference to hearing prosthesis embodiments and more particularly cochlear implant embodiments. However, the disclosed systems, methods, and articles of manufacture are not so limited. Many of the disclosed features and functions described with respect to the cochlear implant embodiments may be equally applicable to other embodiments that may include other types of medial stimulation prostheses including, prosthetic-limb stimulation devices, vibration-based hearing devices, direct acoustic stimulation devices, auditory brain stem implants, or any other type of medical stimulation prosthesis that is configured such that one component generates stimulation commands and transmits the stimulation commands across a data link to another component, which applies or executes the stimulation commands.

Example Hearing Prosthesis Configuration

Figure 1:
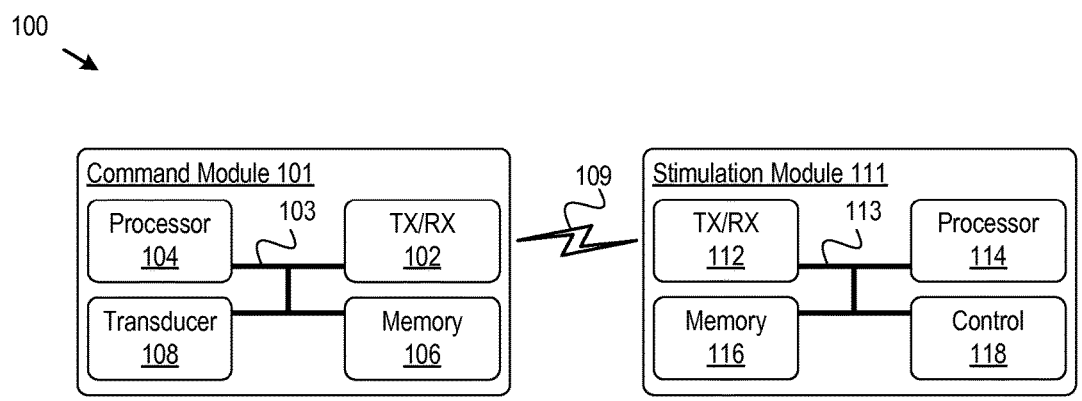
FIG. 1 shows a block diagram of certain selected hearing prosthesis components according to some embodiments of the disclosed systems and methods.

FIG. 1 shows a block diagram of an example hearing prosthesis 100 according to some embodiments of the disclosed systems and methods. In some embodiments, hearing prosthesis 100 is a cochlear implant; however, in other embodiments, hearing prosthesis 100 is another kind of implant, such as a vibration-based hearing device, a direct acoustic stimulation device, or an auditory brain stem implant. The hearing prosthesis shown in FIG. 1 may be implanted into a hearing prosthesis recipient according to any general implant procedure. In some embodiments, hearing prostheses, such as hearing prosthesis 100, have additional or different components than those depicted in FIG. 1; but, for brevity's sake, the configuration depicted in FIG. 1 focuses on a selected set of components that may be helpful to illustrate certain aspects of the disclosed embodiments.

In the embodiment shown in FIG. 1, hearing prosthesis 100 includes a command module 101 and a stimulation module 111. Although not shown in FIG. 1, in some embodiments, the command module 100 is included within an external component assembly that is directly or indirectly attached to the body of the hearing prosthesis recipient, whereas the stimulation module 111 is included within an internal component assembly that is temporarily or permanently implanted in the hearing prosthesis recipient. However, in other embodiments, the command module 100 and the stimulation module 111 are both included within one or more internal component assemblies, each of which are temporarily or permanently implanted in the hearing prosthesis recipient.

The command module 101 is shown as including a transmit/receive sub-module 102, a processor sub-module 104, a memory sub-module 106, and a transducer sub-module 108, all of which may be connected directly or indirectly via circuitry 103. Similarly, the stimulation module 111 is shown as including a transmit/receive sub-module 112, a processor sub-module 114, a memory sub-module 116, and a control sub-module 118, all of which may be connected directly or indirectly via circuitry 113. In some embodiments, the sub-modules of the command module 101 are located on a single integrated circuit, whereas in other embodiments, the sub-modules of the command module 101 are spread out across two or more integrated circuits. Likewise, in some embodiments, the sub-modules of the stimulation module 111 are located on a single integrated circuit, whereas in other embodiments, the sub-modules of the stimulation module are spread out across two or more integrated circuits.

In the embodiment shown in FIG. 1, transducer 108 is configured to detect sound waves and generate an audio signal representative of those sound waves. Transducer 108 may be further configured to transmit to processor 104, via circuitry 103, a generated audio signal that is based on the detected sound waves. Depending on the desired configuration, transducer 108 may be one or more microphones, one or more telecoil induction pickup coils, or some other sound-detection device now known or later developed.

In the embodiment shown in FIG. 1, processor 104 is configured to receive, analyze, and encode an audio signal sent from transducer 108 (or another source) into one or more stimulation commands according to a particular sound-coding strategy. Processor 104 may also be configured to conduct one or more hearing prosthesis system diagnostic tests, analyze the results of the one or more hearing prosthesis system diagnostic tests, and/or implement one or more actions in response to the results of the one or more hearing prosthesis system diagnostic tests. In some embodiments, processor 104 may also be configured to analyze measured responses to stimulation signals generated via the electrodes of the hearing prosthesis 100. Depending on the desired configuration, processor 104 may include one or more processors, including but not limited to, programmable processors, application specific integrated circuits, programmable logic arrays, digital signal processors, and/or other general and/or special purpose processors configured to perform one or more of the functions of the hearing prosthesis 100 as described further below.

In the embodiment shown in FIG. 1, the transmit/receive sub-module 102 is configured to transmit stimulation commands produced by processor 104 to the stimulation module 111. Such transmission is carried out by way of data link 109 and may be of any protocol and format in accordance with a particular sound-coding strategy. In some embodiments, transmit/receive sub-module 102 includes a coil of a transcutaneous energy transfer system along with associated circuitry to drive the coil. However, in other embodiments, transmit/receive module 102 may be any radio-frequency (RF) interface or other wired or wireless communication interface that facilitates data communications.

As a general matter, data link 109 may be any coupling that enables data transmission between the transmit/receive sub-module 102 and the transmit/receive module 112. In some embodiments, data link 109 is a transcutaneous RF inductive link. In other embodiments, data link 109 is any air interface or other wired connection. Further, in some embodiments, e.g., the embodiments depicted in FIGS. 2A-B and 3A-F, data link 109 is a half-duplex data link. A half-duplex data link is a data link across which the command module 101 and the stimulation module do not simultaneously transmit packets. In other embodiments, data link 109 is a full-duplex data link. A full-duplex data link is a data link across which the command module 101 and the stimulation module may simultaneously transmit packets.

In addition to communicatively coupling to transmit/receive sub-module 112, transmit/receive sub-module 102 may communicatively couple to an external fitting system (not shown) by way of another data link (not shown). The transmit/receive sub-module 102 may be configured to send and/or receive information to and/or from the fitting system. For example, in some embodiments, the transmit/receive sub-module 102 is configured to receive configuration or map data from a fitting system. The transmit/receive sub-module 102 may also be configured to send measurement data to the fitting system. In some embodiments, the transmit/receive sub-module 102 may also be configured to send and/or receive data to/from other ancillary devices that are associated with the hearing prosthesis 100.

In the embodiment shown in FIG. 1, memory module 106 includes one or more computer-readable storage media that can be read from, written to, or otherwise accessed by processor 104. In some embodiments, the storage media of the memory module 106 is also read from, written to, or otherwise accessed by a fitting system (not shown). Additionally, the storage media of memory 106 may also be read from, written to, or otherwise accessed by one or more of the transmit/receive sub-module 102 and/or the transducer 108. In some embodiments, the storage media in the memory sub-module 106 is configured to store configuration, or MAP, data for the hearing prosthesis 100 or other programming instructions that facilitate general operation of the hearing prosthesis 100 in accordance with the functions described herein. The storage media of the memory sub-module 106 may also be configured to store the results of one or more diagnostic tests that are initiated, performed, or otherwise controlled in whole or in part by either processor 104 or a fitting system.

The hearing prosthesis 100 shown in FIG. 1 also includes a stimulation module 111, which generally includes functionality similar to that of an internal component assembly. For instance, transmit/receive sub-module 112 may include all or part of the functionality of an internal receiver unit. In some embodiments, the transmit/receive sub-module 112 may be configured to receive over the data link 109 stimulation commands transmitted by command module 101. Depending on the configuration, the transmit/receive sub-module may be the counterpart of transmit/receive sub-module 102 insofar as transmit/receive sub-module 112 may include an internal coil of the noted transcutaneous energy transfer system. In some embodiments, however, transmit/receive sub-module 112 may be any RF interface or other wired or wireless communication interface that facilitates data communications.

Similar to processor 104, processor 114 may include one or more processors, including but not limited to, programmable processors, application specific integrated circuits, programmable logic arrays, digital signal processors, and/or other general and/or special purpose processors configured to perform one or more of the functions of the hearing prosthesis 100, such as operating control sub-module 118, as described further below.

Similar to memory sub-module 106, memory sub-module 116 may include one or more computer-readable storage media that can be read from, written to, or otherwise accessed by processor 114. In some embodiments, the storage media of the memory module 106 may also be read from, written to, or otherwise accessed by a fitting system, such as fitting system 145 in FIG. 1. Additionally, the storage media of memory 106 may also be read from, written to, or otherwise accessed by one or more of the transmit/receive sub-module 112 and/or the control sub-module 118. In some embodiments, the storage media in the memory sub-module 116 may be configured to store configuration, or MAP, data for the hearing prosthesis 100 or other programming instructions that facilitate general operation of the hearing prosthesis 100 in accordance with the functions described herein. The storage media of the memory sub-module 116 may also be configured to store the results of one or more diagnostic tests that are initiated, performed, or otherwise controlled in whole or in part by either processor 114, control sub-module 118, or a fitting system.

Depending on the embodiment, hearing prosthesis 100 may include additional components that are not shown in FIG. 1. For example, in embodiments in which hearing prosthesis 100 is a cochlear implant, the cochlear implant may include an array of two or more electrodes. Typically, the electrodes are positioned along the recipient's cochlea. During operation, the stimulation module 111, in response to receiving one or more stimulation commands from the command module 100, applies via control sub-module 118 one or more electrical signals to the electrode array in order to stimulate the recipient's cochlea. However, as indicated above, depending on the embodiment, an electrode array, or other similar stimulation apparatus, may be positioned along other portions of the recipient, including for example the outer ear, inner ear, middle ear, cranial or facial bones, teeth, or brain stem.

Depending on the embodiment, control sub-module 118 includes circuitry configured to control and manage the electrode array or other similar stimulation apparatus. By way of example, such circuitry may include a signal generation sub-module, a transmit amplifier sub-module, a switching sub-module, a receive amplifier sub-module, and/or a signal measurement sub-module (not shown).

Example Transmission of Stimulation Data and Configuration Data

In practice, in order to facilitate the operation of a hearing prosthesis, two types of data are typically transmitted across data link 109. One type of data is called stimulation data, and another type of data is called configuration data.

In some embodiments, stimulation data is generated by command module 101 and transmitted to stimulation module 111. Generally, stimulation data takes the form of one or more stimulation commands. As described briefly above, in some embodiments, the command module 101, and more particularly, processor 104, analyzes an electrical signal produced by transducer 108 in response to received acoustic signals and generates one or more stimulation commands for transmission to the stimulation module 111 across data link 109.

If the hearing prosthesis includes an electrode array, a stimulation command typically identifies to the stimulation module 111 at least two electrodes from that electrode array between which to apply an electrical signal. In some embodiments, one of the two identified electrodes may already be known by the stimulation module 111 and may not change between successive stimulation commands. Such an electrode is sometimes referred to as the reference electrode and is often omitted from the stimulation command. Additionally, a stimulation command may also identify an amplitude of the electrical signal to apply to the indicated electrodes.

In some embodiments, the command module 101 generates the stimulation commands in accordance with a particular stimulation strategy. A stimulation strategy is a set of rules that define how command module 101 analyzes acoustic signals and generates stimulation commands. If the hearing prosthesis includes an electrode array, the stimulation strategy also dictates to which electrodes to apply electrical signals, the amplitude of such electrical signals, and the order and configuration in which to apply the electrical signals. Command module 101 may use any example stimulation strategy, including Continuous Interleaved Sampling (CIS), Spectral Peak (SPEAK), Advanced Combination Encoder (ACE), or any other suitable stimulation strategy now known or later developed.

In embodiments in which electric currents are applied to one or more pairs of electrodes, the manner in which an electrode pair and corresponding current level is determined is referred to as "mapping." In some embodiments, mapping is performed in the command module 101. In such embodiments, the command module 101 generates stimulation commands, based on the current sound coding strategy, that indicate particular electrode numbers and corresponding current levels to apply between those electrodes. Upon receipt of such stimulation commands, the stimulation module 111 reads and applies the stimulation with no additional processing.

In other embodiments, however, mapping is performed in the stimulation module 111. In such embodiments, the command module 101 generates stimulation commands, based on the current sound coding strategy, that indicate channels and amplitudes. Upon receipt of such stimulation commands, the stimulation module 111 reads the stimulation command and refers to a lookup table (or something similar) to determine the electrode numbers and current levels to apply based on the indicated channel and amplitude. In some embodiments, the lookup table will indicate that a single channel corresponds to multiple electrodes. Further, an amplitude can typically be represented with fewer bits than can a current level. Thus, indicating the single channel and an amplitude in the stimulation command, rather than indicating multiple electrode numbers and current levels, may allow for smaller stimulation commands to be sent across the data link 109. Generally, this represents one form of data compression.

Figure 2A:
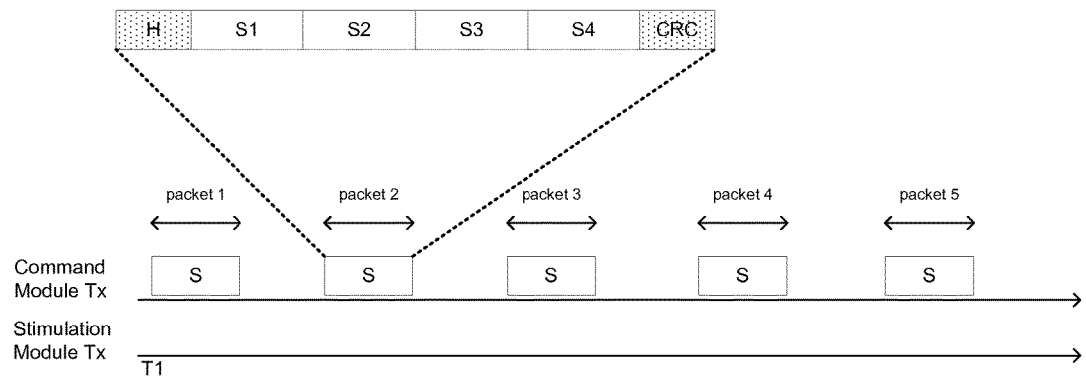
FIGS. 2A-2B show example timing diagrams depicting the transmission of stimulation data and configuration data in a half-duplex link embodiment.

To facilitate orderly data transmission, command module 101, in some embodiments, arranges generated stimulation commands into packets and transmits the packets across data link 109. FIG. 2A is an example timing diagram that depicts the transmission of five stimulation data packets. Generally, transmissions originating at the command module 101 and directed to the stimulation module 111 are called "forward-channel" transmission and are said to occur on a "forward channel," whereas transmissions originating at the stimulation module 111 and directed to the command module 101 are called "reverse channel" transmissions and are said to occur on a "reverse channel." The stimulation data packets in FIG. 2A are denoted with an S. As shown in FIG. 2A, stimulation data packets are fixed in length and sent at regular intervals (e.g., 1000 per second). However, packets may be of varying lengths and may be sent at varying intervals.

Moreover, as illustrated in FIG. 2A, packets are typically divided into four slots denoted S1, S2, S3, and S4. Header information, denoted H, precedes the first slot and cyclic redundancy check information, denoted CRC, follows the fourth slot. In some embodiments, packets may be divided into more or fewer slots and a different or even no type of error correction may be used.

Although not depicted in FIG. 2A, on the forward channel, individual bits may be encoded in any number of different ways. For example, in some embodiments, bits are encoded using a token scheme. Table 1 shows two example token encoding schemes, a "6/3" token scheme and a "10/8" token scheme. In embodiments that incorporate a 6/3 token scheme, three data bits are encoded into six encoded bits called "cells." And according to Table 1, there are six RF "cycles" (sometimes referred to RF signal oscillations) per cell. Thus, according to Table 1, using the 6/3 encoding scheme translates to a data rate of 416 kilobits per second (kbps). Alternatively, in embodiments that incorporate a 10/8 token scheme, eight bits are encoded into ten cells. And according to Table 1, there are four RF cycles per cell when using the 10/8 encoding scheme. Thus, according to Table 1, using this scheme translates to a data rate of 1000 kbps. The 6/3 scheme provides for more error correction than the 10/8 scheme but results in a lower data rate. Other encoding schemes are possible as well.

TABLE 1

| Encoding Scheme Type | RF Cycles per Cell | Bit Rate |
| --- | --- | --- |
| 6/3 | 6 | 416 kbps |
| 10/8 | 4 | 1000 kbps |

Similarly, Table 2 shows two example encoding schemes used for reverse channel transmission. In some embodiments, bits transmitted on the reverse link are not encoded using tokens and are transmitted using double pulse telemetry. In such embodiments, each pulse pair is separated by 15 microseconds. Thus, according to Table 2, such embodiments will result in a reverse channel data rate of 66 kbps. In other embodiments, bits transmitted on the reverse link are encoded using a 10/8 token scheme, similar to that discussed above, and transmitted using single pulse telemetry. In such embodiments, each pulse is separated by 5 microseconds. Thus, according to Table 2, such embodiments will result in a bit rate of 160 kbps. Other encoding schemes are possible as well.

TABLE 2

| Encoding Scheme Type | Pulse Type | Bit Rate |
| --- | --- | --- |
| None | Double | 66 kbps |
| 10/8 | Single | 160 kbps |

As indicated above, in addition to stimulation data transmitted by command module 101, in some embodiments, command module 101 transmits configuration data to stimulation module 111. Generally, configuration data is any data that is not stimulation data. Configuration data may be transmitted by command module 101 or stimulation module 111. In one example, configuration data is transmitted by command module 101 and contains an indication to the stimulation module 111 to change at least a portion of the current stimulation strategy. Additionally or alternatively, such configuration data may also include data that indicates at least one operational parameter to change (e.g., the reference electrode), the format of the stimulation commands, some other operational parameter, or a request for a measurement or readout value from the stimulation module 111. In another example, configuration data is transmitted by stimulation module 111 and contains a measurement, readout value, or some other data flag, perhaps in response to a request from command module 101.

Figure 2B:
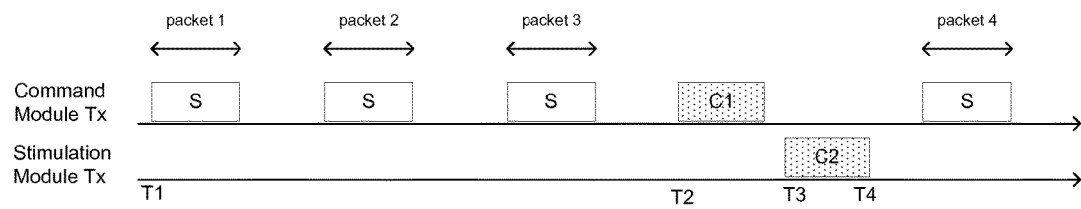

FIG. 2B is another example timing diagram depicting an example transmission of stimulation and configuration data. At time T1, the command module begins transmission of stimulation data. In particular, command module 101 transmits three stimulation packets, each of which is denoted S, to stimulation module 111. At time T2, command module 101 interrupts transmission of the stimulation data to begin transmission of a block of configuration data, denoted C1, to stimulation module 111. At time T3, stimulation module 111 begins transmission of a block of configuration data, denoted S2, back to command module 101. Transmission of the configuration data stops at time T4, at which point the transmission of stimulation data begins again.

In the example illustrated in FIG. 2B, the transmission of stimulation data is interrupted during the transmission of configuration data. Thus, during the transmission of configuration data, the hearing prosthesis might not be applying stimulation signals to the recipient and the recipient would therefore not be experiencing a sound sensation.

During the ordinary transmission of stimulation data (i.e., stimulation data packets that are not interrupted by transmission of configuration data), there is typically a delay between successive stimulation packets. Usually, this delay does not amount a gap or delay in stimulation signals applied to the recipient. This may be the case for any number of reasons. For example, this could be due to compression of the stimulation data. Alternatively, it could be due to the sparse nature of stimulation signals, as dictated by the current stimulation strategy. For example, the amount of time taken to transmit a given stimulation data packet may be less than the amount of time corresponding to stimulation signals applied to the recipient. Other reasons for delays between successive stimulation packets are possible as well.

If the amount of configuration data is relatively small, then the period of interruption of stimulation signals might also be small, or nonexistent, which usually will not pose a serious interruption in corresponding sound sensation for the recipient. However, with the increasing sophistication of various hearing prostheses, it is possible that the amount of configuration data communicated back and forth between a command module and a stimulation module will increase significantly. It is also possible that stimulation packets could increase in size and command a greater share of the data link 109 bandwidth. Such increases may be problematic. For example, stimulation signal gaps of up to 800 microseconds are not noticeable by some recipients if the sound being transmitted to the recipients is speech. For sounds that are pure tones, 400 microsecond stimulation signal gaps are not noticeable to some recipients, but 800 microsecond stimulation signal gaps are noticeable. To address this situation, and potentially others, disclosed herein are methods and systems for dividing a block of configuration data into fragments and transmitting the fragments separately across the data link 109.

Figure 3A:
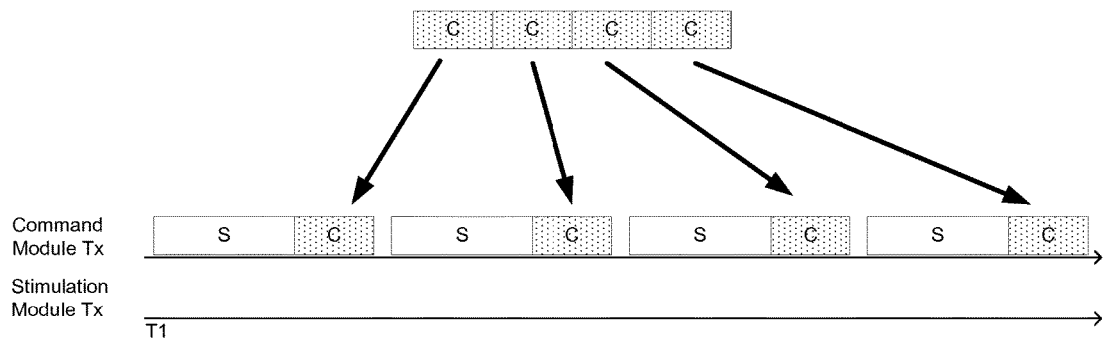
FIGS. 3A-F show example timing diagrams depicting the transmission of configuration data fragments according to some half-duplex link embodiments of the disclosed systems and methods.

In accordance with one example embodiment, as illustrated by the timing diagram in FIG. 3A, instead of transmitting configuration data in one large block, command module 101 divides the block of configuration data into fragments and appends each fragment to a different stimulation packet. As shown in FIG. 3A, command module 101 divides the block of configuration data into four fragments and appends each fragment to one of four stimulation packets. Command module 101 then transmits to stimulation module 111 each stimulation packet, which contains one fragment of configuration data.

Upon receiving the stimulation packets with appended configuration data fragments, stimulation module 111 reassembles the configuration data fragments into readable configuration data and processes it accordingly. For example, in accordance with one embodiment, the fragments are reassembled and checked for errors (e.g., via a cyclic redundancy check or some other error checking process). If an error is detected, the stimulation module 111 requests the retransmission of the erroneous fragment or fragments. Any amount of configuration data subject to retransmission would be transmitted in accordance with the same configuration data transmission process as described herein.

In the embodiment depicted in FIG. 3A, individual configuration data fragments are appended at the end of individual stimulation data packets. However, in other embodiments, individual configuration data fragments may be appended to individual stimulation data packets at other places, including for example the beginning or the middle of the individual packet.

In the embodiment depicted in FIG. 3A, individual configuration data fragments are appended to consecutive stimulation data packets. However, other embodiments are not so limited. Generally, configuration data is not as time sensitive as stimulation data might be in some embodiments. In some situations, as noted above, it is possible that a recipient would experience a noticeable interruption in sound sensation should stimulation signals applied to the recipient be delayed by even 1 millisecond. Conversely, a hearing prosthesis recipient is not likely to experience any noticeable interruption in sound sensation or other negative operational experiences should configuration data be delayed by the methods and systems for dividing a block of configuration data into fragments and transmitting the fragments separately across the data link 109 described herein. Consequently, in embodiments different from the embodiment depicted in FIG. 3A, individual configuration data fragments may be appended to non-consecutive stimulation data packets.

For example, in some embodiments, a hearing prosthesis transmits at least one stimulation data packet with a configuration data fragment appended thereto. Subsequently, the hearing prosthesis transmits one (or more) stimulation data packets with no configuration data fragments appended thereto. And subsequent to that transmission, the hearing prosthesis again transmits at least one stimulation data packet with a configuration data fragment appended thereto. In embodiments such as this, the hearing prosthesis can afford to send configuration data fragments at irregular intervals because the configuration data is not as time sensitive as the stimulation data.

Figure 3B:
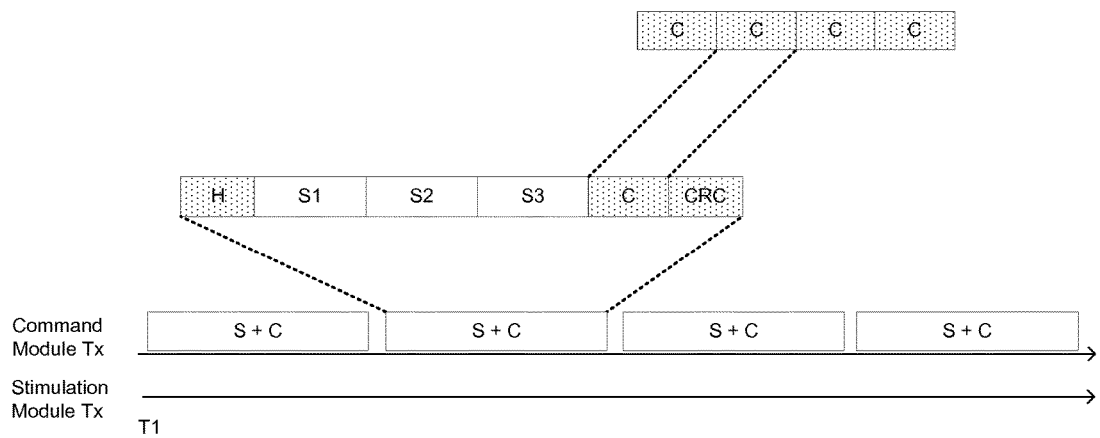

FIG. 3B is a timing diagram depicting an example format of a configuration data fragment appended to a stimulation packet, the combination of which is referred to as a "joint stimulation and configuration data packet" and denoted S+C. As shown in FIG. 3B, the stimulation portion of the joint stimulation and configuration data packet contains three slots, denoted 51, S2, and S3, instead of the four slots depicted in FIG. 2A. Each slot contains one or more stimulation commands (not shown), as described above with respect to FIG. 2A. The stimulation portion of the joint stimulation and configuration data packet also contains header information, denoted H, and CRC information, denoted CRC. In the space usually occupied by the fourth slot, S4, is one of the configuration data fragments, denoted C.

Figure 3C:
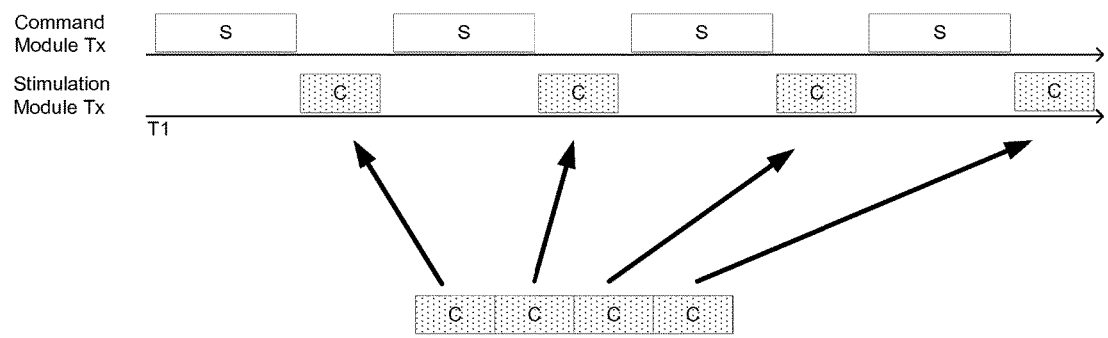

FIG. 3C is another example timing diagram depicting an example embodiment in which the stimulation module 111 transmits configuration data fragments. As shown in FIG. 3C, stimulation module 111 divides a block of configuration data into four fragments and after reception of a stimulation data packet, stimulation module 111 transmits one of the configuration data fragments to command module 101. Upon receiving the configuration data fragments, command module 101 reassembles the fragments in a manner similar to that described above with respect to command module 101.

Depending on the embodiment, command module 101 or stimulation module 111 may divide a block of configuration data into any suitable number of data fragments of any suitable size and append each fragment to a suitable number of stimulation packets. For example, in some embodiments, command module 101 first determines a number of stimulation packets (e.g., ten packets) over which to transmit configuration data fragments. Command module 101 then divides a block of configuration data into that determined number of substantially equally-sized fragments. Finally, command module 101 appends the configuration data fragments to stimulation data packets and transmits the appended packets across data link 109.

In other embodiments, command module 101 first calculates a desired size for a configuration data fragment. Command module 101 then divides a block of configuration data into a plurality of fragments of the calculated size. Finally, command module 101 appends the configuration data fragments to stimulation data packets and transmits the appended packets across data link 109.

Command module 101 may calculate a desired size of a configuration data fragment in any number of different ways. In one example embodiment, command module 101 calculates a size of a configuration data fragment and divides the block of configuration data into fragments of the calculated size. In this embodiment, the calculated size generally falls between a lower bound and an upper bound. The lower bound is the size of the gap in between two successive stimulation commands. And the upper bound is the size of a configuration data fragment that would delay the ordinary transmission of stimulation commands so as to cause a noticeable delay in perceived sound sensation by the implant recipient. Thus, configuration data fragments that are the size of the lower bound do not delay stimulation data packets because they fit in the gaps between successive stimulation data packets. And configuration data fragments that are the size of the upper bound delay stimulation data packets but not so much as to cause a noticeable delay in perceived sound sensation by the implant recipient.

The size of a configuration data fragment that causes a noticeable delay in perceived sound sensation may be different for different hearing prosthesis recipients. For instance, some recipients may be able to withstand a relatively long delay in the ordinary transmission of stimulation data commands before noticing an interruption of perceived sound, whereas other recipients may be not be able to tolerate much of a delay in the ordinary transmission of stimulation commands at all before noticing an interruption of perceived sound. Therefore, such a calculated size may be determined by a series of tests conducted by an audiologist or other similarly-trained specialist during a fitting session.

In another example embodiment, command module 101 calculates a size of a configuration data fragment by determining an amount of space in a stimulation packet that is unused. Depending on several factors, including the communication protocol, the current stimulation strategy, and the type and amount of error correction, there may be an amount of unused space in each data packet. Command module 101 may divide a block of configuration data into fragments of a particular size such that each fragment fits into the unused space of a stimulation packet. In this manner, there may be little to no delay in transmitting stimulation packets as a result of transmitting configuration data and therefore little to no interruption in perceived sound by the hearing prosthesis recipient.

In accordance with one example calculation of the amount of unused space in a stimulation packet, command module 101 first determines the number of packets sent per second (e.g., 1000 packets per second), which is dictated by the current transmission protocol. Next, the command module 101 determines the number of pulses per second and the number of bits in each stimulation command (e.g., 16 k pulses per second and 13 bits per stimulation command), both of which are dictated by the current stimulation strategy. At one stimulation command per pulse, multiplying the bits per stimulation command by the pulses per second and dividing by the packet rate (e.g., 13*16 k/1 k=208) yields the number of stimulation bits per packet. Adding the number of bits used for header information and error correction information per packet (e.g., 40 bits of overhead) yields the total number of bits per stimulation packet (e.g., 208+40=248). Command module 101 then determines the amount of time it takes to transmit each bit according to the particular stimulation strategy (e.g., 3.75 μs per bit) and multiplies that number by the total number of bits per stimulation packet yielding the total time occupied by stimulation data in each stimulation packet (e.g., 3.75*248=930 μs). Finally, subtracting the total time occupied by stimulation data in each packet (e.g., 930 μs) as well as any built-in delay between successive packets (e.g., 10 μs) from the total time it takes to transmit a stimulation packet (e.g., 1000 μs) yields the amount of unused space in each data packet (e.g., 1000 μs–930 μs–10 μs=60 μs). Of course, these parameters are merely examples and other parameters are possible as are other methods of determining the amount of unused space in a stimulation packet, both of which depend on the particular embodiment.

In yet another example embodiment, the stimulation module 111 calculates a size of a configuration data fragment by reading data specified in the header of a preceding stimulation data packet. In some embodiments, the command module 101 specifies in the header portion of a stimulation command the size of the gap that immediately follows the stimulation command. Thus, upon receipt of a stimulation packet, the stimulation module 111 reads the header portion of the stimulation packet to determine the upcoming gap size. The stimulation module 111 then calculates a size of a configuration data fragment to fit within the specified gap size.

Figure 3D:
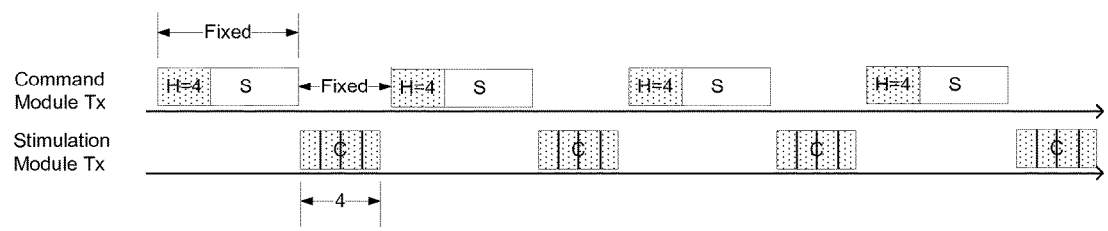

For example, FIG. 3D is another timing diagram depicting another example embodiment of transmission of stimulation and configuration data. In the embodiment depicted by FIG. 3D, each stimulation data packet is a fixed size, and therefore each gap size is a fixed size. As depicted, the header information specifies a gap size in which a configuration data fragment of four bits could fit. Thus, each configuration data fragment transmitted by the stimulation module 111 to the command module 101 is four bits.

Figure 3E:
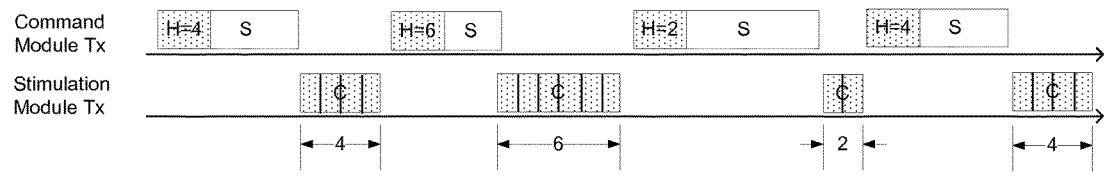

FIG. 3E is another timing diagram depicting another example embodiment of transmission of stimulation and configuration data. In the embodiment depicted by FIG. 3D, each stimulation data packet is not a fixed size, and therefore each gap size is not fixed. As depicted, the header information of the first stimulation packet specifies a gap size in which a configuration data fragment of four bits could fit. Thus, the configuration data fragment that follows the first stimulation data packet is four bits. As further depicted, the second stimulation data packet is smaller than the first. Accordingly, the header information of the second stimulation packet specifies a gap size in which a configuration data fragment of six bits could fit. Thus, the configuration data fragment that follows the second stimulation data packet is six bits. As further depicted, header information of the third stimulation data packet indicates a gap size in which a two-bit configuration data fragment could fit; consequently, the configuration data fragment following this stimulation data packet is two bits. Finally as depicted, header information of the fourth stimulation data packet indicates a gap size in which a four-bit configuration data fragment could fit; consequently, the configuration data fragment following this stimulation data packet is four bits. Other sizes of stimulation data packets, gaps, and configuration data fragments are possible as well, as are other ways to indicate such gap sizes.

Generally, the command module 101 is able to determine the gap sizes between successive stimulation data packets because the command module 101 can determine the type of stimulation strategy currently employed. For example, in embodiments in which mapping is performed in the stimulation module 111, the command module 101 recognizes that the stimulation data packets are smaller and therefore calculates the gap size between successive stimulation commands.

Figure 3F:
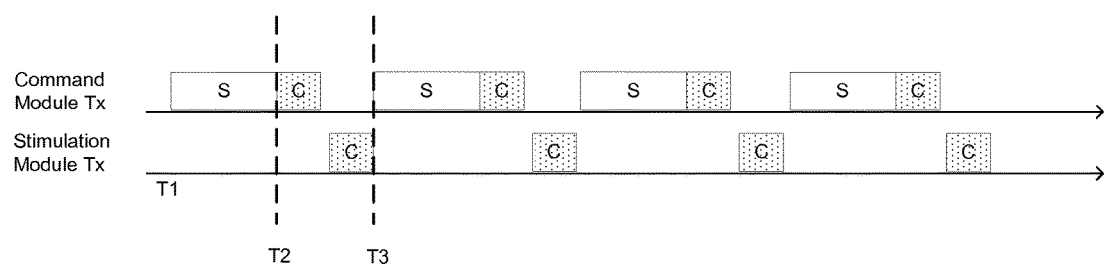

In still another example embodiment, the command module 101 and/or stimulation module 111 share the gap size for transmission of a configuration data fragment. For example, FIG. 3F is another timing diagram depicting another example embodiment of transmission of stimulation and configuration data. In the embodiment depicted by FIG. 3F, command module 101 and stimulation module 111 share the time in between two successive stimulation data packets in order to transmit configuration data fragments. In FIG. 3F, this time is represented by the gap in between time T2 and time T3. In one embodiment, stimulation data packets are transmitted at a rate of about 1000 per second. And an individual stimulation data packet is transmitted in about 400 microseconds (e.g., the time between time T1 and time T2), thus leaving a gap of about 600 microseconds in between any two stimulation data packets (e.g., the time between time T2 and time T3). In this embodiment, the command module 101 divides its block of configuration data into fragments that can each be transmitted in about 300 microseconds. Likewise, stimulation module 111 divides its block of configuration data into fragments that can each be transmitted in about 300 milliseconds, thus substantially filling the gap between two successive stimulation data packets with configuration data fragments. Of course, these times are merely examples and in other embodiments, stimulation data packets are transmitted at other suitable rates, individual stimulation data packets are transmitted in other suitable times, and gaps of other suitable lengths exist between individual stimulation data packets. Generally, each of these parameters is dictated by the stimulation strategy.

Moreover, in other embodiments, command module 101 and stimulation module 111 share the gap between successive stimulation data packets in unequal proportions. For example, if the gap length is 600 milliseconds, the command module 101 may divide its block of configuration data into fragments that can each be transmitted in about 500 milliseconds, whereas the stimulation module 111 may divide its block of configuration data into fragments that can each be transmitted in about 100 milliseconds. In still other embodiments, one of the command module 101 and the stimulation module 111 may not transmit any configuration data fragment in a particular gap, whereas the other of the command module 101 and the stimulation module 111 may divide its block of configuration data into fragments that can each be transmitted in all or part of the particular gap.

Example Operation

Figure 4:
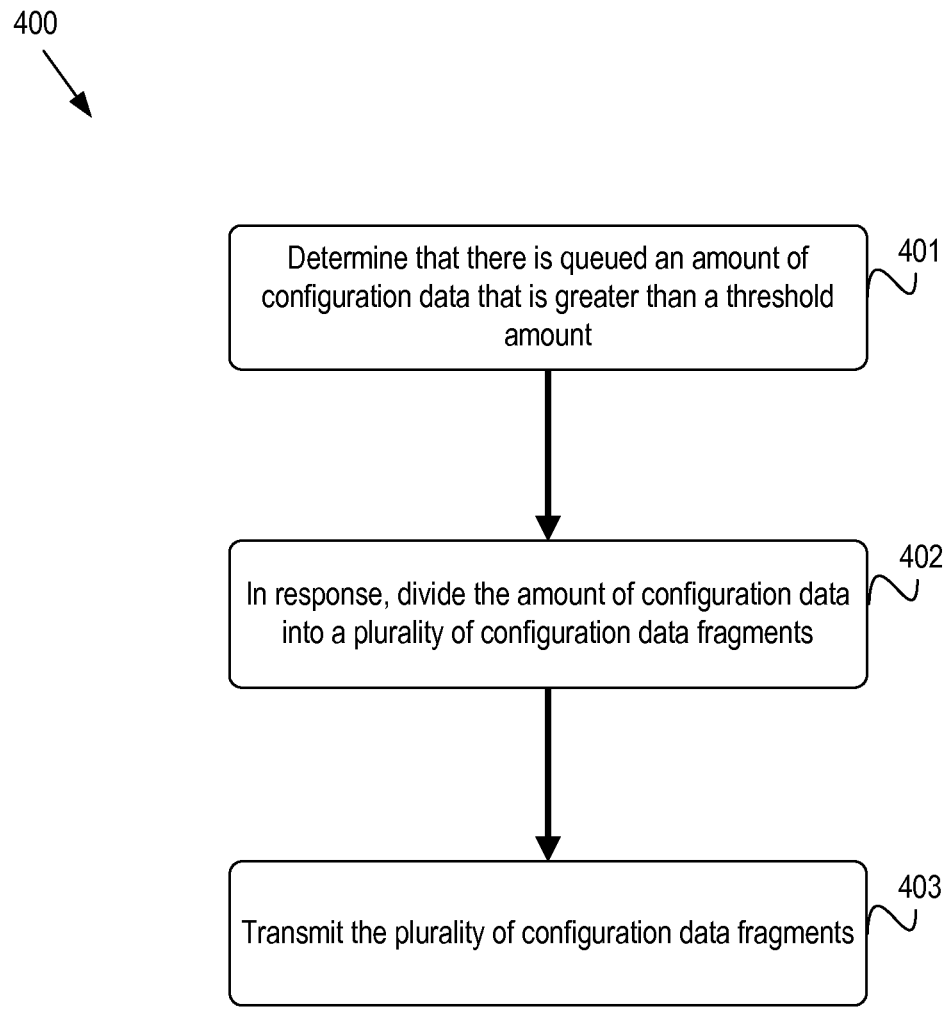
FIG. 4 is a flow chart depicting an example method for transmitting configuration data according to an example embodiment.

FIG. 4 is a flowchart depicting an example method 400 that may be used by a hearing prosthesis to divide a block of configuration data into fragments and transmit the fragments separately across a data link, in accordance with some embodiments. The method 400 may be implemented by one or more of the components of hearing prosthesis 100, such as by one or more sub-modules of command module 101 or by one or more sub-modules of stimulation module 111.

Method 400 begins at block 401, where the hearing prosthesis determines that there is a block of configuration data to send across data link 109. When there is a block of configuration data to send across data link 109 but not yet sent, that block is sometimes said to be "queued." Thus, at block 401, hearing prosthesis 100 determines that there is queued an amount of configuration data.

In some embodiments, hearing prosthesis 100 determines that there is queued any amount of configuration data. However, in other embodiments, hearing prosthesis determines that there is queued an amount of configuration data that is greater than a threshold amount of configuration data. In one embodiment, the threshold amount of configuration data is based on an amount of data such that, if it were sent across the data link 109 in one continuous block, it would cause a delay in the transmission of stimulation data and thereby potentially cause an undesirable interruption in perceived sound by the hearing prosthesis recipient.

At block 402, the hearing prosthesis, in response to the determining at block 401, divides the amount of configuration data into a plurality of configuration data fragments. The hearing prosthesis divides the queued block of configuration data into fragments in accordance with any of the above-described embodiments.

Finally, at block 403, the hearing prosthesis transmits the plurality of configuration data fragments separately across the data link 109. As described above, in one embodiment, the command module 101 appends the configuration data fragments to stimulation packets and transmits the stimulation packets across the data link 109 to stimulation module 111. In another embodiment, stimulation module 111 transmits a configuration data fragment to command module 101 upon receiving a stimulation packet from command module 101.

Figure 5:
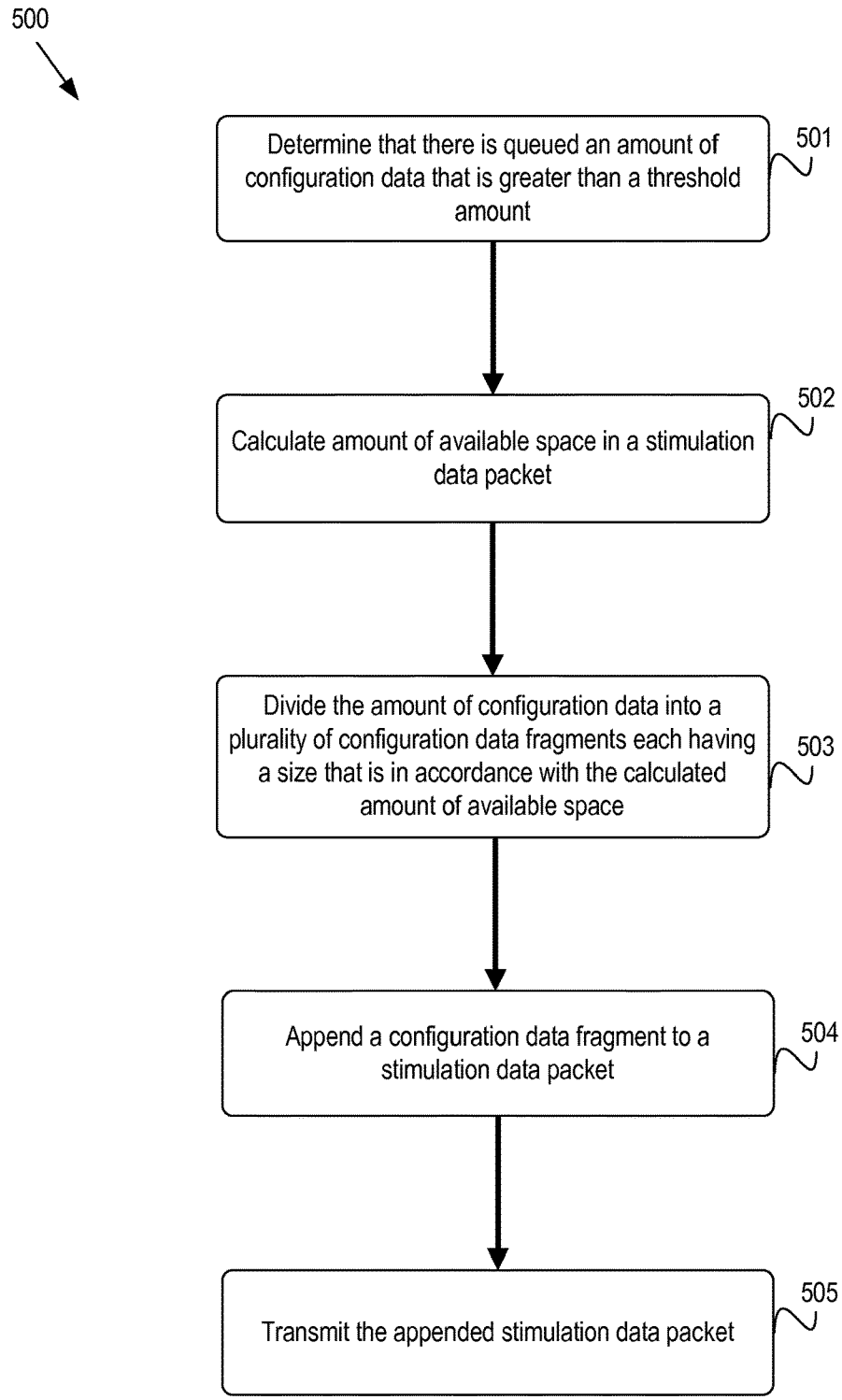
FIG. 5 is another flow chart depicting another example method for transmitting configuration data according to another example embodiment.

FIG. 5 is another flowchart depicting another example method 500 that incorporates additional functions for a hearing prosthesis to divide a block of configuration data into fragments and transmit the fragments separately across a data link, in accordance with some embodiments. Method 500 begins at block 501 where, like at block 401 in method 400, the hearing prosthesis determines that there is queued an amount of configuration data that is greater than a threshold amount of configuration data. The hearing prosthesis may make this determination in accordance with the above description of block 401.

At block 502, the hearing prosthesis calculates the amount of available space in a stimulation data packet. For example, as described above in one embodiment, the hearing prosthesis determines that it transmits 1000 data packets per second. Therefore, the hearing prosthesis transmits one stimulation packet in 1000 µs. As further described in the above example, in each stimulation packet there is 10 µs of built-in delay before transmission of a subsequent packet. The stimulation strategy and the communication protocol used in the example embodiment dictated that all the stimulation data in one packet be sent in 930 µs. Thus, the hearing prosthesis calculates that there is 1000 µs−930 µs−10 µs=60 µs of available time per packet in which space to transmit configuration data. Again, these are merely example parameters and in practice, other parameters are possible and will depend on the transmission protocol and stimulation strategy in use.

At block 503, the hearing prosthesis divides the amount of queued configuration data into a plurality of fragments in which each fragment has a size that is in accordance with the calculated amount of available space in a stimulation data packet. In accordance with the example described above, the hearing prosthesis divides the configuration data into fragments that can be transmitted in 60 las (or less). If, for example, the hearing prosthesis is utilizing a transmission protocol that dictates each bit be sent in 3.75 las, then the hearing prosthesis may divide the configuration data into fragments of 16 bits.

At block 504, the hearing prosthesis appends a configuration data fragment to a stimulation packet according to any of the methods described herein. Finally, at block 505, the hearing prosthesis transmits across data link 109 the appended stimulation data packet.

Computer Readable Media Implementations

In some embodiments, the disclosed features and functions of the systems, methods, and algorithms shown and described herein may be implemented as computer program instructions encoded on a computer readable media in a machine-readable format.

Figure 6:
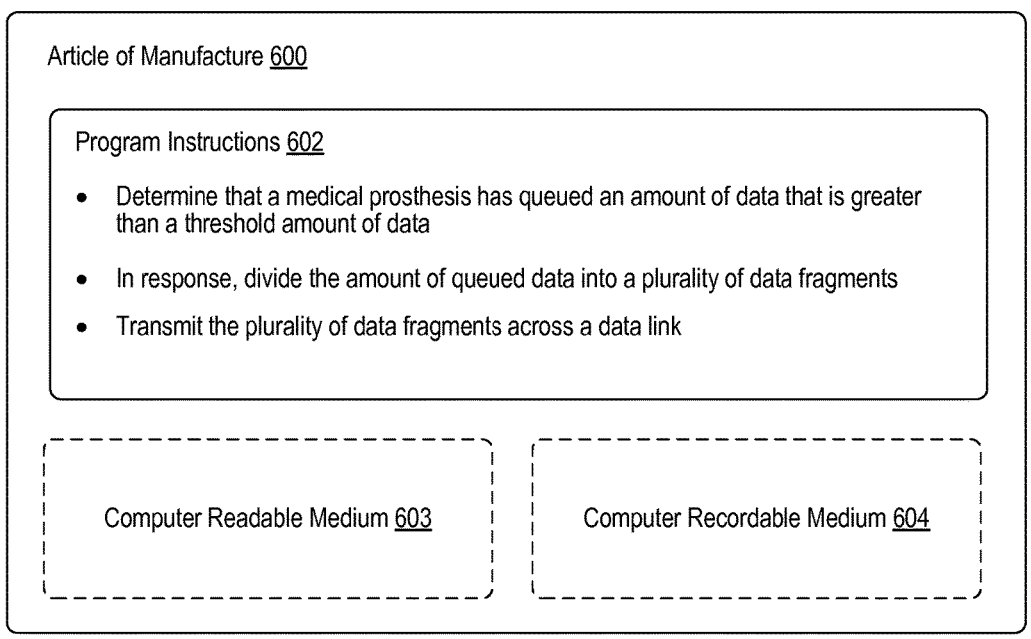
FIG. 6 shows an example of an article of manufacture including computer readable media with instructions for transmitting configuration data according to an example embodiment.

FIG. 6 shows an example of an article of manufacture 600 including computer readable media with instructions for causing one or more processors to execute a method for dividing a block of configuration data into fragments and transmitting the fragments separately across a data link according to some embodiments of the disclosed systems and methods. FIG. 6 shows a schematic illustrating a conceptual partial view of an example article of manufacture 600 that may include computer program instructions 602 for executing a computer process on a computing device, arranged according to at least some embodiments described herein.

In some examples, the article of manufacture 600 may include a computer-readable medium 603, such as, but not limited to, a hard disk drive, a Compact Disc (CD), a Digital Video Disk (DVD), a digital tape, flash memory, etc. In some implementations, the article of manufacture 600 may include a computer recordable medium 604, such as, but not limited to, a hard disk drive, a Compact Disc (CD), a Digital Video Disk (DVD), a digital tape, flash memory, etc.

The one or more programming instructions 602 may be, for example, computer executable and/or logic implemented instructions. In some embodiments, processor 104 of command module 101 or processor 114 of stimulation module 111, alone or in combination with one or more other processors associated with the hearing prosthesis 100, may be configured to perform various operations, functions, or actions to implement the features and functionality of the disclosed systems and methods based at least in part on the programming instructions 602.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A medical prosthesis system, comprising:
an external component assembly comprising:
   a transmit/receive sub-module configured for communication with an internal component assembly across a transcutaneous communication link, wherein the external component assembly is configured to be coupled to a recipient of the medical prosthesis system and the internal component assembly is configured to be implanted in the recipient;
a memory; and
one or more processors configured to:
   queue a block of configuration data in the memory,
   determine that a queued amount of configuration data is greater than a predetermined threshold amount of configuration data, and
   in response to determining that the queued amount of configuration data is greater than a predetermined threshold amount of configuration data, divide the queued amount of configuration data into a plurality of configuration data fragments,
wherein the transmit/receive sub-module is configured to transmit the plurality of configuration data fragments across the transcutaneous communication link to the internal component assembly.

2. The medical prosthesis system of claim 1, wherein the predetermined threshold amount of configuration data is a predetermined recipient specific threshold amount of configuration data.

3. The medical prosthesis system of claim 1, wherein the predetermined threshold amount of configuration data corresponds to an amount of configuration data that would cause an interruption in transmission of stimulation data across the transcutaneous communication link that is perceivable by the recipient of the medical prosthesis system.

4. The medical prosthesis system of claim 1, wherein the one or more processors are configured to:
calculate a size of a configuration data fragment, and divide the block of configuration data into fragments of the calculated size.

5. The medical prosthesis system of claim 4, wherein to calculate a size of a configuration data fragment, the one or more processors are configured to:
determine a current sound coding strategy,
based on the current sound coding strategy, determine a gap size between successive stimulation data packets, and
specify the determined gap size in header information embedded in data transmitted across the transcutaneous communication link.

6. The medical prosthesis system of claim 1, wherein to divide the queued amount of configuration data into a plurality of configuration data fragments, the one or more processors are configured to:
calculate an amount of available space in a stimulation data packet transmitted from the transmit/receive sub-module to the internal component assembly across the transcutaneous communication link, and
divide the queued amount of configuration data to provide an individual configuration data fragment that is sized to fit within the calculated amount of available space, wherein the individual configuration data fragment is one of the plurality of configuration data fragments.

7. The medical prosthesis system of claim 1, wherein to divide the queued amount of configuration data into a plurality of configuration data fragments, the one or more processors are configured to:
calculate an amount of space between two successive stimulation data packets transmitted from the transmit/receive sub-module to the internal component assembly across the transcutaneous communication link, and
divide the queued amount of configuration data to provide an individual configuration data fragment that is sized to fit within the calculated amount of space, wherein the individual configuration data fragment is one of the plurality of configuration data fragments.

8. The medical prosthesis system of claim 7, wherein to calculate an amount of space between two successive stimulation data packets, the one or more processors are configured to:
read header data specified in a stimulation data packet; and
calculate, based on the header data, a minimum size of a configuration data fragment that, if transmitted between successive stimulation data packets, would not delay a transmission of either of the two successive stimulation data packets.

9. The medical prosthesis system of claim 7, wherein the calculated amount of space between two successive stimulation data packets is a function of a current stimulation strategy.

10. The medical prosthesis system of claim 1, wherein the one or more processors are further configured to:
append individual configuration data fragments of the plurality of configuration data fragments to payloads of individual corresponding stimulation data packets to generate a plurality of appended stimulation data packets, and
cause the internal component assembly to transmit the plurality of appended stimulation data packets to the transmit/receive sub-module.

11. The medical prosthesis system of claim 1, wherein the one or more processors are configured to:
receive a plurality of stimulation data packets from the internal component assembly, and
transmit one of the configuration data fragments in response to receiving each stimulation data packet in the plurality of stimulation data packets.

* * * * *